United States Patent
Kokovidis et al.

(10) Patent No.: US 12,274,568 B2
(45) Date of Patent: Apr. 15, 2025

(54) TILT RESISTANT STAND

(71) Applicant: DRÄGERWERK AG & CO. KGAA, Lubeck (DE)

(72) Inventors: Georgios Kokovidis, Waltham, MA (US); Christopher Kokovidis, Waltham, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 286 days.

(21) Appl. No.: 17/880,249

(22) Filed: Aug. 3, 2022

(65) Prior Publication Data

US 2023/0065777 A1   Mar. 2, 2023

Related U.S. Application Data

(60) Provisional application No. 63/238,678, filed on Aug. 30, 2021.

(51) Int. Cl.
*A61B 50/24* (2016.01)

(52) U.S. Cl.
CPC .................................. *A61B 50/24* (2016.02)

(58) Field of Classification Search
CPC ...................................................... A61B 50/24
See application file for complete search history.

(56) References Cited

U.S. PATENT DOCUMENTS

| | | | |
|---|---|---|---|
| 2008/0283534 A1* | 11/2008 | Paz | A61B 50/36 220/737 |
| 2013/0270799 A1 | 10/2013 | Schmutzer | |
| 2014/0117635 A1* | 5/2014 | Ninomiya | A61B 8/4405 280/35 |
| 2015/0328398 A1 | 11/2015 | Divito | |
| 2016/0263311 A1 | 9/2016 | Chepurny | |
| 2017/0258547 A1* | 9/2017 | Karasina | A61B 50/24 |
| 2019/0090964 A1* | 3/2019 | Rosenberg | B25J 5/007 |
| 2023/0090944 A1* | 3/2023 | Rotem | A61B 34/30 700/245 |

OTHER PUBLICATIONS

PCT/IB2022/057426 International Search Report and Written Opinion of the International Searching Authority, dated Oct. 31, 2022, 13 pages.

* cited by examiner

*Primary Examiner* — Erez Gurari
(74) *Attorney, Agent, or Firm* — NOLTE LACKENBACH SIEGEL

(57) ABSTRACT

A tilt resistant stand for medical devices may include a base with casters and an upright support with a mounting portion for a medical device. A stand for medical devices can be resistant to tilting by having a gravitational centroid that is substantially vertically aligned with the geometric centroid of the base for enhanced stability, where the gravitational centroid is defined as a combined center of gravity of the medical device stand and any medical devices mounted thereto and the geometric centroid of the base is defined as a horizontal planar region having the casters as vertices. The gravitational centroid may be substantially vertically aligned with the geometric centroid due to a horizontal offset between the mounting portion and the geometric centroid.

18 Claims, 9 Drawing Sheets

TILT RESISTANT STAND

CROSS REFERENCE TO RELATED APPLICATIONS

The present application claims priority to and the benefit of U.S. Prov. Pat. App. Ser. No. 63/238,678, which was filed on Aug. 30, 2021, for all purposes, including the right of priority, which application is hereby incorporated herein by reference in its entirety.

BACKGROUND

Technical Field

The present disclosure generally relates to ambulatory stands. In particular, the disclosure relates to ambulatory stands for medical devices, including patient monitors and other devices for the provisioning of medical care.

Description of the Related Art

This section of this document introduces information about and/or from the art that may provide context for or be related to the subject matter described herein and/or claimed below. It provides background information to facilitate a better understanding of the various aspects of the that which is claimed below. This is a discussion of "related" art. That such art is related in no way implies that it is also "prior" art. The related art may or may not be prior art. The discussion in this section of this document is to be read in this light, and not as admissions of prior art.

In hospitals or other patient-care settings, monitoring and tracking a patient's condition, including vital signs, respiratory information, and the like, are used to deliver timely and appropriate medical care to the patient. Numerous types of sensors have been developed that detect one or more aspects of a patient's condition and transmit signals representative of the detected conditions to monitoring devices. These monitoring devices can then show the patient's condition with visual readouts and/or reveal specific conditions through audible alerts. Additionally, devices for providing medical care to patients, such as by aiding in respiration, dispensing fluids, gasses, pharmaceuticals, and other substances related to medical treatment may be commonly used in hospitals and other patient-care settings.

Such medical devices may be kept close to a patient due to the tubes, sensor wires, or other lines connecting the medical devices to the patient. In cases where a patient moves in a medical facility, such as walking down a hospital hallway, it is a common practice to mount the medical devices on a stand with casters, which can enable the stand to be moved with the patient. This permits the patient to move about without unnecessarily interrupting care and monitoring.

BRIEF DESCRIPTION OF THE DRAWINGS

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Figure 1:
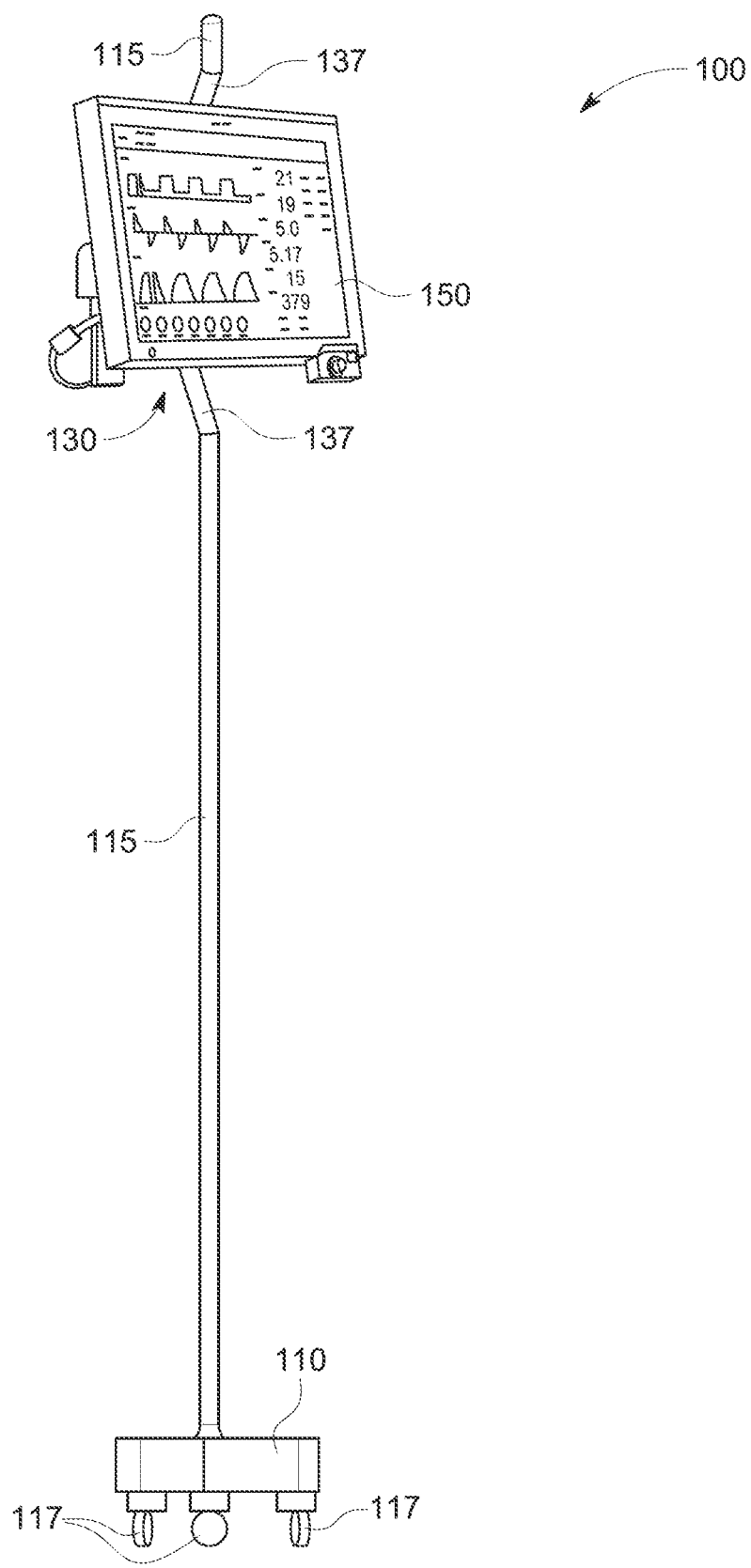
FIG. 1 is a perspective view of an ambulatory medical device stand having a medical device mounted thereto according to one embodiment of the present disclosure.

While the invention is susceptible to various modifications and alternative forms, the drawings illustrate specific examples herein described in detail by way of example. It should be understood, however, that the description herein of specific examples is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Illustrative examples of the subject matter claimed below will now be disclosed. In the interest of clarity, not all features of an actual implementation are described in this specification. It will be appreciated that in the development of any such actual implementation, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Medical device stands may have one or more medical devices mounted thereto at a height several feet above the floor. As such, these stands are at risk of tipping. To mitigate the risk of tipping, typical medical device stands are made with a wide, heavy base. The width of the base, having casters spread relatively far apart, may reduce the risk of tipping. Likewise, the weight of the base, having a relatively low center of gravity, may reduce the risk of tipping. However, a heavy medical device stand with a wide base may be cumbersome and awkward to move. The width of the stand base might pose a tripping hazard to the patient and/or others walking by the stand. The weight of the stand base may fatigue the patient or caregivers as they move the medical device stand.

According to various embodiments, the present disclosure is directed to mobile, ambulatory medical device stands. In particular, a mobile, ambulatory medical device stand may hold one or more medical devices that are mounted thereto. In the present disclosure, the term "medical device" may refer to patient monitors and monitoring devices for monitoring, tracking, displaying, and/or recording any number of patient vital signs or other data. Examples of such data may include data from a variety of tests or monitoring including but not limited to: heart rate, electrocardiogram, respiration, ST segment analysis from an electrocardiogram, end-tidal $CO_2$, oxygen saturation, electroencephalogram, temperatures, blood pressure, arrhythmia, other data related to a patient's care, condition, or status, and/or other relevant information that may be useful or relevant to medical service providers. The monitors may further display lab data, scans such as X-ray scans, MRI scans, and other data relating to the patient and/or the patient's medical care.

One embodiment of the present disclosure comprises a mobile, ambulatory medical device stand for a medical device. The medical device stand includes an upright support, a base, and at least three casters. The upright support defines a mounting portion upon which a medical device may be mounted. The upright support has a gravitational centroid defined as a combined center of gravity of the upright support and the medical device. The upright support vertically extends from the base. The casters are structurally engaged with the base. The casters define a horizontal plane and a geometric centroid. The geometric centroid is substantially vertically aligned with the gravitational centroid of the upright support.

Another embodiment of the present disclosure comprises a method of assembling a medical apparatus. The method includes providing a mobile, ambulatory medical device stand for a medical device and mounting the medical device to a mounting portion of the medical device stand. The medical device stand includes an upright support, a base, and at least three casters. The upright support defines a mounting portion upon which the medical device may be mounted. The upright support vertically extends from the base. The casters define a horizontal plane and a geometric centroid. The mounting portion is horizontally offset from the geometric centroid. The medical device is mounted to the mounting portion in such a way that the medical device and the upright support combine to form a gravitational centroid. The gravitational centroid is defined as a combined center of gravity of the upright support and the medical device. The geometric centroid is substantially vertically aligned with the gravitational centroid.

Another embodiment of the present disclosure comprises a mobile, ambulatory medical device stand assembly. The medical device stand assembly includes an upright support defining a mounting portion upon which a medical device may be mounted, a medical device, a first gravitational centroid, a base, at least three casters, and a medical device mounted at the mounting portion. The first gravitational centroid is defined as a combined center of gravity of the upright support and the medical device. The upright support vertically extends from the base. The casters are structurally engaged with the base. The casters define a horizontal plane and a geometric centroid. The geometric centroid is substantially vertically aligned with the gravitational centroid of the upright support.

In the present disclosure, the term "medical device" may also further refer to devices for providing medical treatment to a patient. Such medical devices may include, but are not limited to, ventilators or other respiratory aids, gas delivery systems, anesthesia or drug delivery systems, fluid delivery systems, and other devices that may be employed by medical service providers or hospital employees in the medical care, treatment, and therapy of patients.

It is to be understood that in the present disclosure, the term "medical device" may refer any number of types of patient monitoring devices or systems and/or medical treatment devices and/or medical therapy devices that are capable of being mounted to a medical device stand as described herein, capable of providing ambulatory and/or mobile treatment, therapy, or monitoring of a patient. In general, such medical devices may be small and light enough to be portable. However, medical devices may be substantially larger or smaller than those depicted in the accompanying drawings.

According to various embodiments of the present disclosure, a mobile, ambulatory medical device stand may carry one or more medical devices mounted thereon, while permitting ambulatory movement of a patient to whom the one or more medical devices may be connected. In particular, the medical devices may be connected to the patient by various types of tubes, sensors wires, or the like. The medical devices may be mounted to the medical device stand at mounting portions at heights that are customizable and configurable according to the circumstances and needs of the patient and/or medical providers, or as may be appropriate for each situation.

As ambulatory medical device stands, embodiments of the present disclosure may be rolled by a patient and/or next to a patient as the patient moves about, for example down hallways within a hospital or other medical facility. The medical device stand may accompany a patient who is walking, traveling by wheelchair, or pushed in a bed.

In embodiments of the present disclosure, medical devices mounted to a medical device stand may be mounted such that each medical device and its respective upright support exhibit a combined gravitational centroid that is located so as to provide stability to the medical device stand. In other embodiments, medical devices mounted to a medical device stand may be mounted such that the combined gravitational centroid of all medical devices and their respective upright supports is located so as to provide stability to the medical device stand. When one or medical devices are mounted to a medical device stand, the resulting combination may be referred to in the present disclosure as a "stand assembly" or a "medical device stand assembly."

Embodiments of a medical device stand according to the present disclosure comprise a base. One or more upright supports, on which mounting portions are located, extend vertically from the base. A base can typically provide stability to the medical device stand by providing multiple points of contact with the floor or other ground surface. In embodiments, these points of contact comprise caster wheels structurally engaged with the base. While any number of casters may be included, embodiments may typically have three, four, or five casters, as such quantities of casters may provide sufficient stability to the base while maintaining a satisfactory degree of lightness to the medical device stand. In some embodiments, three or five casters are preferred for stability and maneuverability purposes.

According to embodiments, the casters define a horizontal planar region. In some cases, the horizontal planar region comprises a polygonal shape having vertices that correspond to the casters. In the present disclosure, the "geometric centroid" of the base is the arithmetic mean position of the vertices of that horizontal planar region. As would be understood by a person of ordinary skill having the benefit of this disclosure, a larger horizontal planar region can result in increased stability of the medical device stand. However, some practicalities may suggest that it is preferable to have a medical device stand base that is fairly limited in width. For example, it may be preferable that the medical device stand base is not so wide that it may likely impede or trip the patient, medical care providers, or other people that are walking next to the medical device stand.

Stability of a medical device stand may be enhanced by substantially vertically aligning the gravitational centroid of all medical devices on the medical device stand and the medical device stand itself with the geometric centroid of the base of the medical device stand. In various embodiments, the respective gravitational centroid of each individual medical device on the medical device stand is substantially vertically aligned with the geometric centroid of the base of the medical device stand.

In the present disclosure, the term "vertically aligned" means that the objects in question lie on the same vertical axis. In other words, two objects that are vertically aligned are positioned such that one object is directly overhead or that the respective vertical axes of the objects in question overlap or intersect each other. In the present disclosure, "substantially vertically aligned" means that the objects in question are vertically aligned with each other or nearly vertically aligned with each other.

Figure 2:
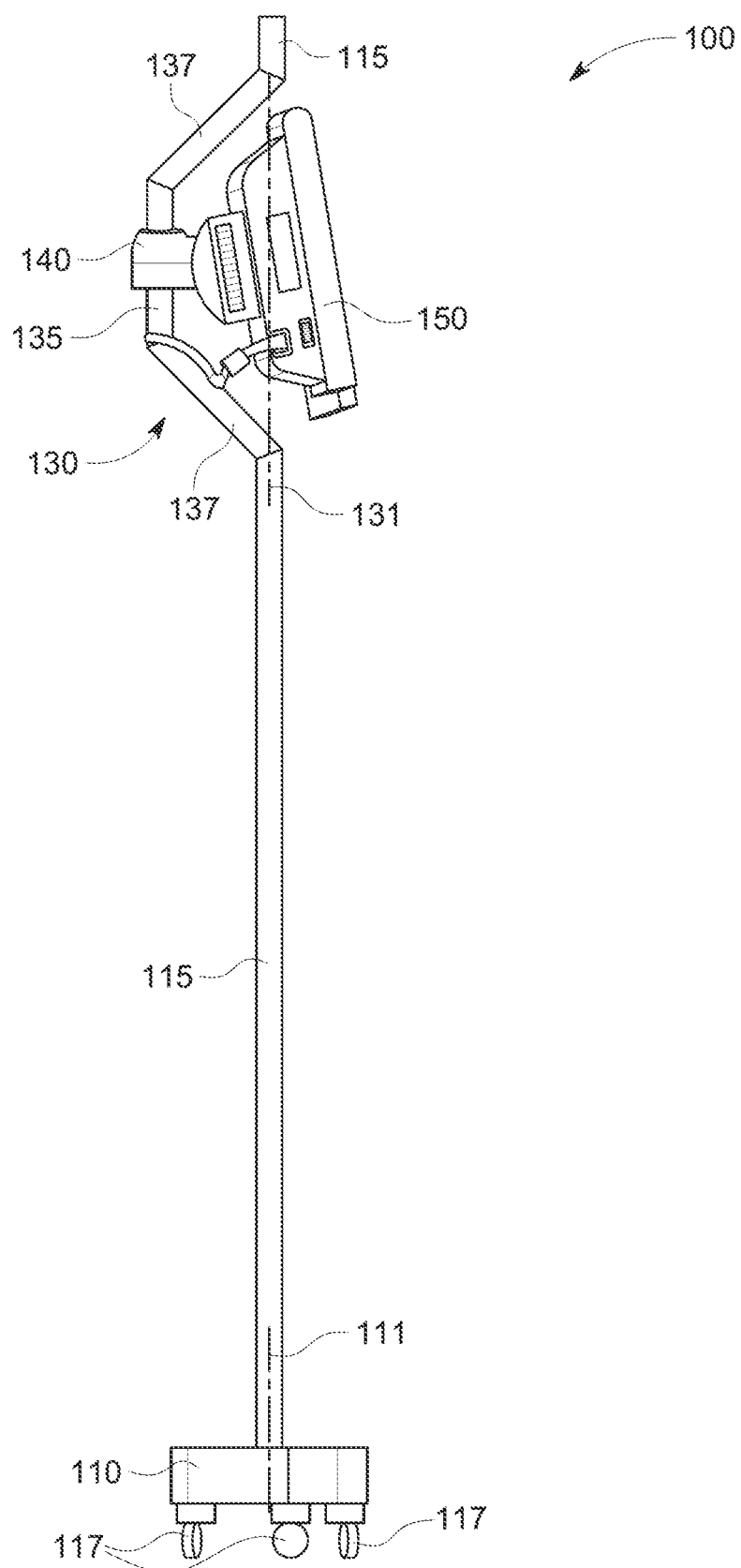
FIG. 2 is a side view of the ambulatory medical device stand of FIG. 1.

Referring to FIG. 1, one embodiment of a medical device stand 100 comprises a base 110 and an upright support 130. A medical device 150 is mounted to upright support 130 that extends vertically from base 110 at an end of vertical extension 115 that is a part of upright support 130. As shown in FIG. 2, a mounting portion 135 is on upright support 130, mounting portion 135 being horizontally offset from the geometric centroid 111 of base 110. The horizontal offset of mounting portion 135 allows the combined gravitational centroid 131 of medical device 150 and upright support 130 to be substantially vertically aligned with the geometric centroid of base 110. In one embodiment, a single mounting portion 135 is on upright support 130. In other embodiments, multiple mounting portions 135 are on upright support 130.

Embodiments of upright support 130 further comprise a connecting member 137 and a mounting member 140. In various embodiments, connecting members 137 can connect vertical extension 115 to mounting portion 135. Connecting members 137 may be selected to provide a desired horizontal offset to suit the width, depth, and/or weight distribution of one or more medical devices 150. As such, connecting members 137 may maintain a combined gravitational centroid 131 substantially vertically aligned with the geometric centroid of base 110, thereby maintaining the stability of medical device stand 100.

As depicted in FIG. 2, embodiments of connecting members 137 create a horizontal offset for mounting portion 135 by the incline of connecting members 137. The angle of inclination and length of connecting members 137 can be selected to determine the horizontal offset of upright support 130. Other embodiments comprise connecting members 137 having various sizes and shapes. Some embodiments of connecting members 137 comprise curved portions, while other embodiments have no inclined portion. One embodiment of connecting member 137 comprises one or more horizontal connecting members 137 (not shown) connecting vertical extension 115 to upright support 130. In embodiments, upright support 130 and connecting members 137 form a vertical span between vertical extensions 115. The size of the vertical span may be just large enough to accommodate medical device 150 or multiple medical devices situated therein.

Some embodiments of upright support 130 comprise mounting member 140 rather than mounting medical device 150 directly to the mounting portion 135 of the vertical extension 115. In embodiments, medical device 150 is secured at mounting portion 135 via mounting member 140. Different embodiments of mounting member 140 comprise a length appropriate for the medical device; the length being adapted to position medical device 150 in such a way to substantially align gravitational centroid 131 of medical device 150 and upright support 130 with the geometric centroid 111 of base 110. In some embodiments, the length of mounting member 140 may be customized to match the weight distribution of medical device 150. For example, medical device 150 having a center of gravity closer to its front may call for a shorter mounting member 140, while a different medical device 150 having a center of gravity closer to its rear may call for a longer mounting member 140.

Figure 3:
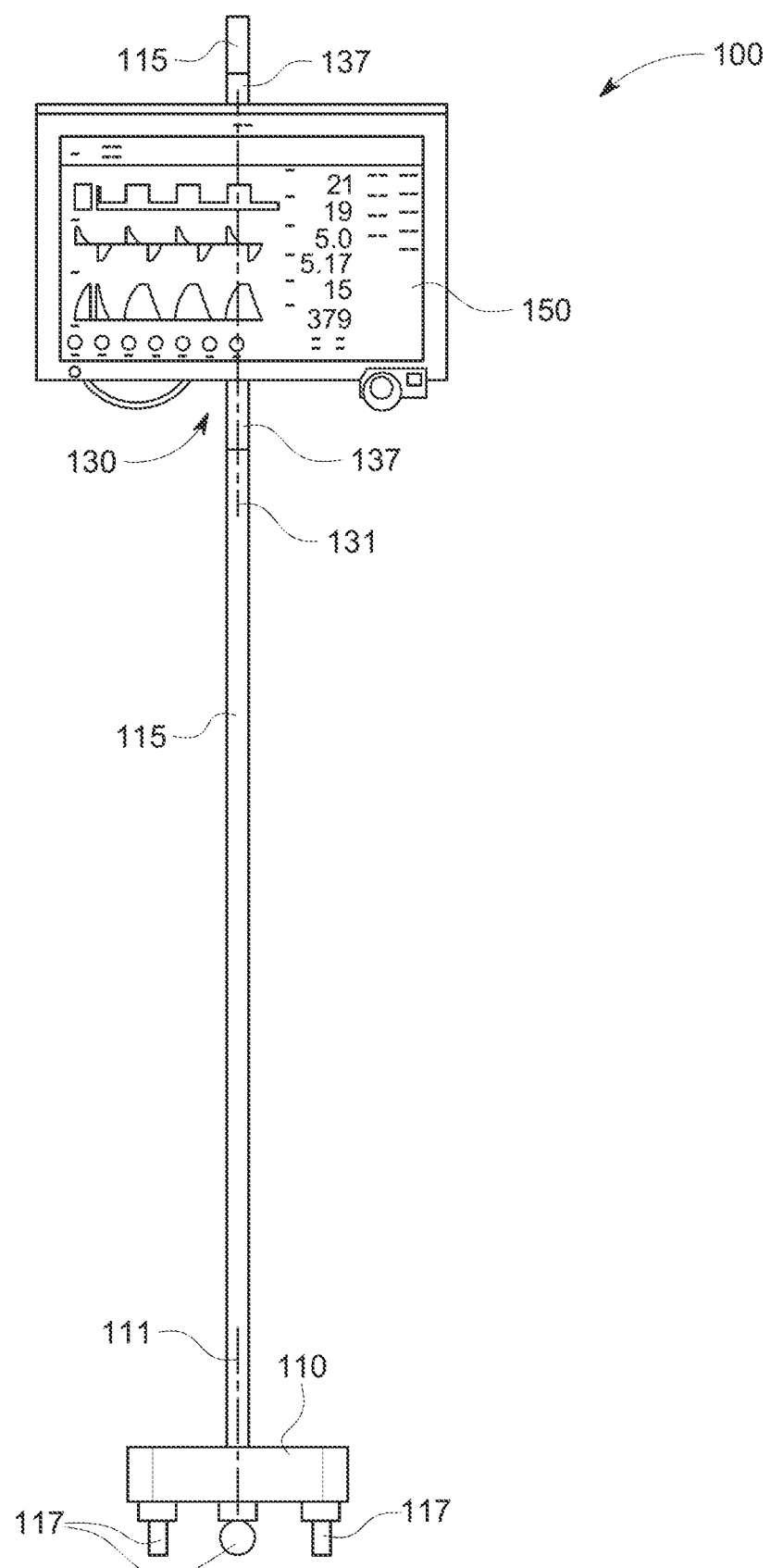
FIG. 3 is a view of the ambulatory medical device stand of FIG. 1 and FIG. 2.

Referring to FIG. 3, the embodiment depicted shows medical device 150 mounted to medical device stand 100 with a left/right orientation that is approximately centered over base 110. However, in other embodiments, medical device 150 may have a center of gravity that is off-center; in such cases, the medical device can be mounted more to the left or to the right relative to medical device stand 100 and base 110 to compensate for the off-center center of gravity of that particular medical device 150 in order to substantially vertically align gravitational centroid 131 of that medical device, combined with its upright support, with the geometric centroid 111 of base 110. Accordingly, in various embodiments, mounting hardware and/or mounting member 140 may be customized for various types of medical devices 150 to allow for right/left mounting adjustment to compensate for the medical device weight distribution.

In various embodiments of the present disclosure, mounting member 140, shown in FIG. 2, is removably attached to upright support 130 at mounting portion 135. As such, one embodiment of medical device stand 100 comprises a modular assembly that can be assembled to meet the specifications of a specific medical device 150; in particular, the weight distribution of one or more medical devices may call for customized horizontal placement relative to base 110 in order to substantially vertically align the combined gravitational centroid 131 of medical device(s) 150 and upright support 130 with geometric centroid of base 110.

Embodiments of mounting member 140 are configured to attach to upright support 130 and provide a mounting point for one or more medical devices 150. Various embodiments of mounting member 140 can secure to upright support 130 by a variety of mechanisms, including but not limited to a friction fit, a clamping mechanism, and bolts or like hardware. In other embodiments, mounting member 140 is held in place on a collar (not shown) on upright support 130 by gravity. In some embodiments, mounting member 140 comprises a mounting arm, plate, bracket, or frame that is secured to upright support 130. The mounting plate, bracket, or frame can secure to medical device 150 to place medical device 150 in position to result in the desired weight distribution. In some embodiments, medical device 150 can be mounted to mounting member 140 by fasteners such as bolts, nuts and/or washers. In other embodiments, medical device 150 can be mounted to mounting member 140 by a snap fit into the mounting member.

As depicted in the figures, embodiments of the present disclosure comprise casters 117 structurally engaged with base 110. In some embodiments, casters 117 include swiveling wheels. In other embodiments, casters 117 include rigid wheels. In various embodiments, casters 117 are mounted to the underside of base 110. Casters 117 define the geometric centroid of the base 110, the geometric centroid being the centroid of a base region having casters 117 as vertices. The stability of medical device stand 100 may be determined by the extent of casters 117 relative to gravitational centroid 131.

By substantially aligning gravitational centroid 131 with geometric centroid 111 of base 110, the moment of inertia of medical device stand 100, and any components or medical devices 150 attached thereto, may be maximized. The moment of inertia of medical device stand 100 may be defined as the amount of torque needed to tilt medical device stand 100 by rotating it about one or more casters 117.

Figure 4:
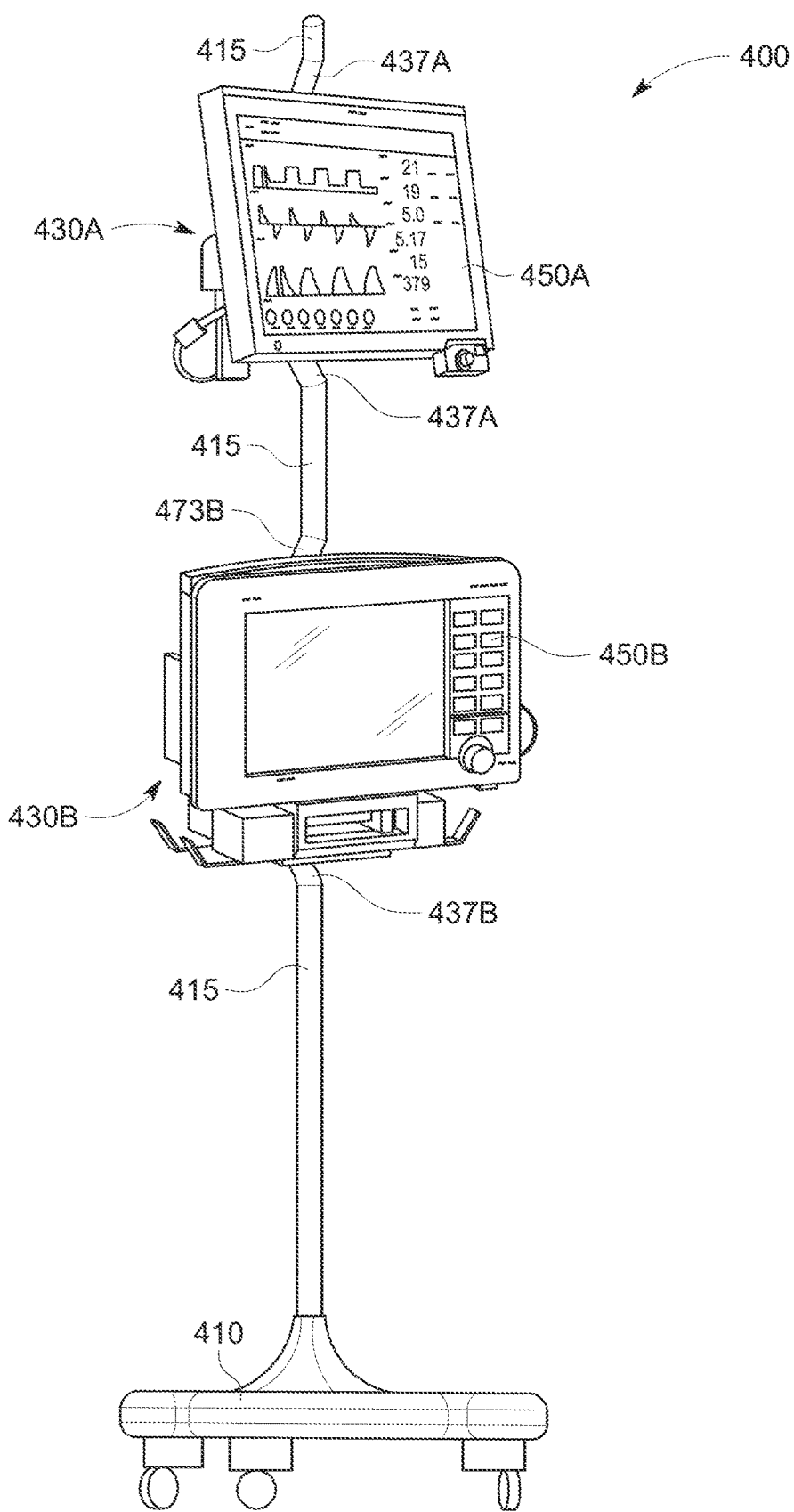
FIG. 4 is a perspective view of an ambulatory medical device stand having multiple medical devices mounted thereto according to one embodiment of the present disclosure.
Figure 5:
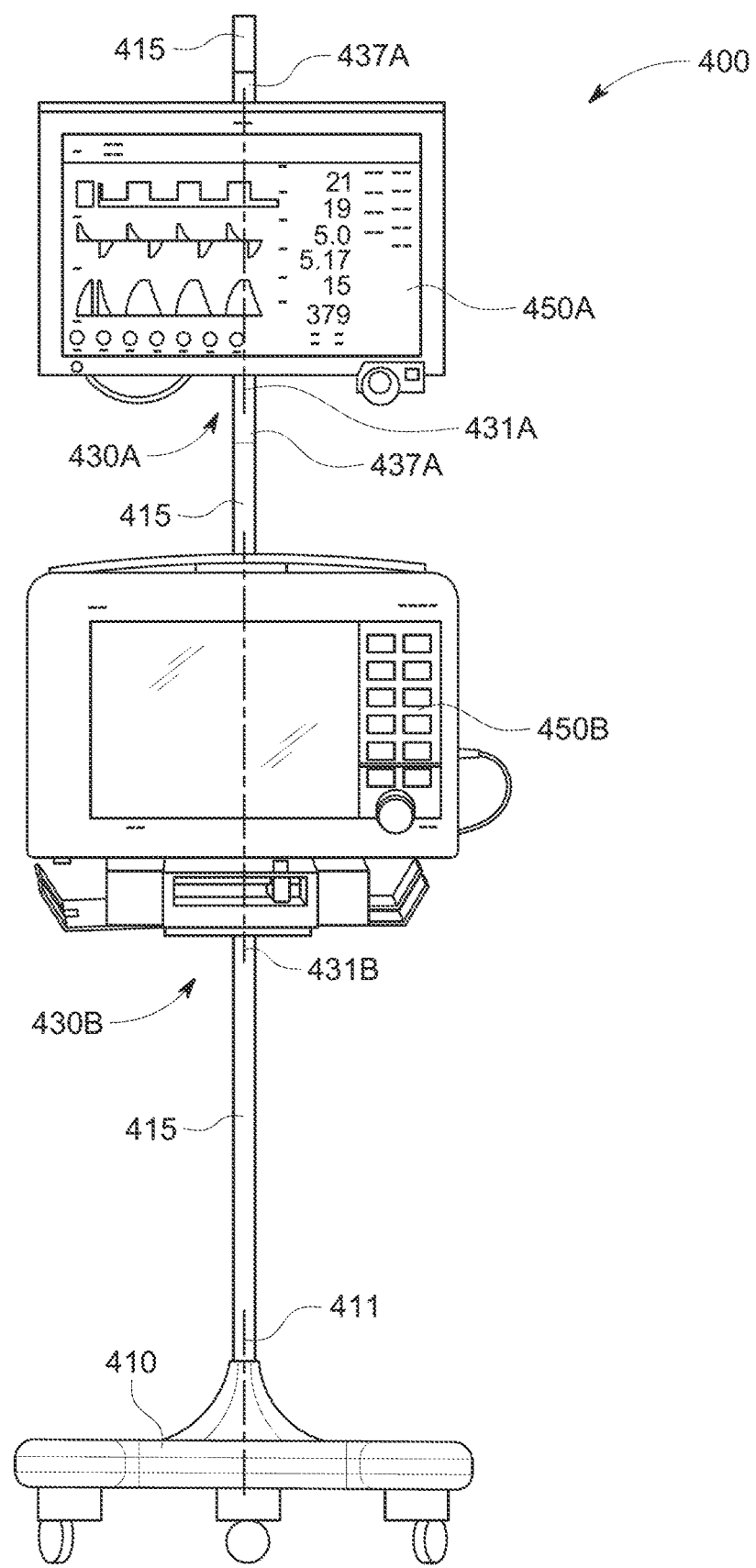
FIG. 5 is a view of the ambulatory medical device stand of FIG. 4 having multiple medical devices mounted thereto.
Figure 6:
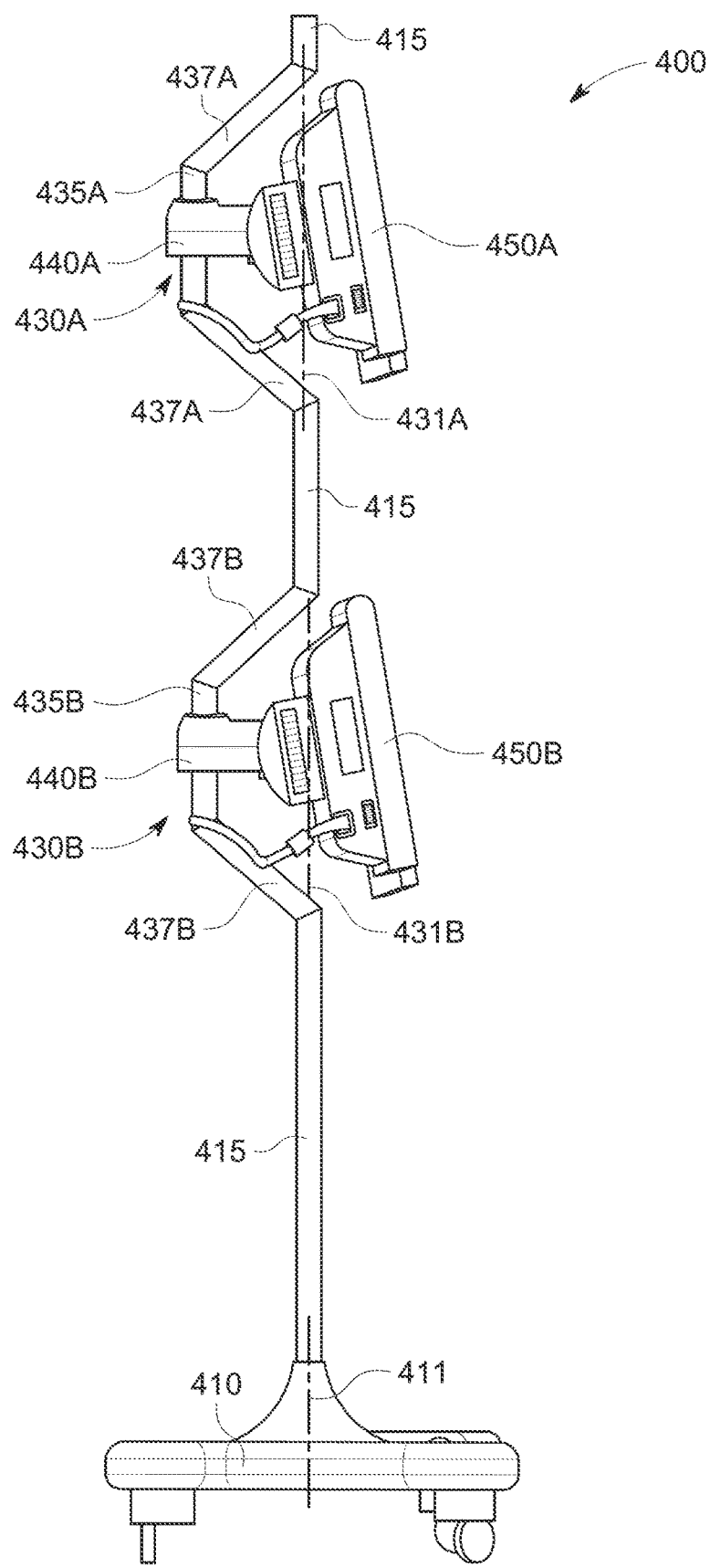
FIG. 6 is a side view of the ambulatory medical device stand of FIG. 4 and FIG. 5 having multiple medical devices mounted thereto.

Referring now to FIGS. 4-6, embodiments of the present disclosure have multiple medical devices 450A, 450 B mounted to medical device stand 400. Upright supports 430A, 430B extend vertically from base 410 at ends of vertical extensions 415. Mounting portions 435A, 435B are located on respective upright supports 430A, 430B and provide a location on which medical devices 450A, 450B can be mounted. In embodiments, each mounting portion 435A, 435B can hold multiple medical devices. In embodiments, each upright support 430A, 430B is horizontally offset from the geometric centroid 411 of base 410, such that a first gravitational centroid 431A of medical device 450A and upright support 430A and a second gravitational centroid 431B of medical device 450B and upright support 430B are substantially vertically aligned with geometric centroid 411 of base 410. Upright support 430A comprises mounting portion 435A, connecting member 437A, and mounting member 440A. Upright support 430B comprises mounting portion 435B, connecting member 437B, and mounting member 440B. As set forth above with respect to FIGS. 1-3, the embodiment depicted in FIGS. 4-6 may enhance or maintain stability of medical device stand 400 by maintaining respective gravitational centroids 431A, 431B substantially vertically aligned with geometric centroid 411 of base 410. In some embodiments, upright support 430A and/or upright support 430B comprise multiple mounting portions 435A, 435B where multiple medical devices 450A, 450B can be mounted. In such cases where multiple medical devices 450A, 450B are mounted to corresponding mounting portions 435A, 435B, respective gravitational centroids 431A, 431 B are defined as combined centers of gravity of the respective upright supports 430A, 430B and all respective medical devices 450A, 450B mounted thereto.

In other embodiments, a combined gravitational centroid is defined as the combined gravitational centroid of medical devices 450A, 450B and upright supports 430A, 430B. The combined gravitational centroid is substantially vertically aligned with geometric centroid 411 of base 410.

Embodiments of the present disclosure comprise assemblies of modular elements, such that a medical device stand may be assembled with components that result in a medical device stand with desirable characteristics such as stability, weight distribution, height, medical device placement, and quantity or size of mounting portions. The stability of a modular medical device stand may be customized by selecting connecting members and mounting members that result in a horizontal offset of each mounting portion relative to the medical device stand base such that the gravitational centroid of the medical devices, combined with the gravitational centroid of the corresponding upright supports, is substantially vertically aligned with the geometric centroid of the base. In some embodiments, multiple medical devices are mounted to each mounting portion. In some embodiments, each upright support comprises multiple mounting portions.

Figure 7:
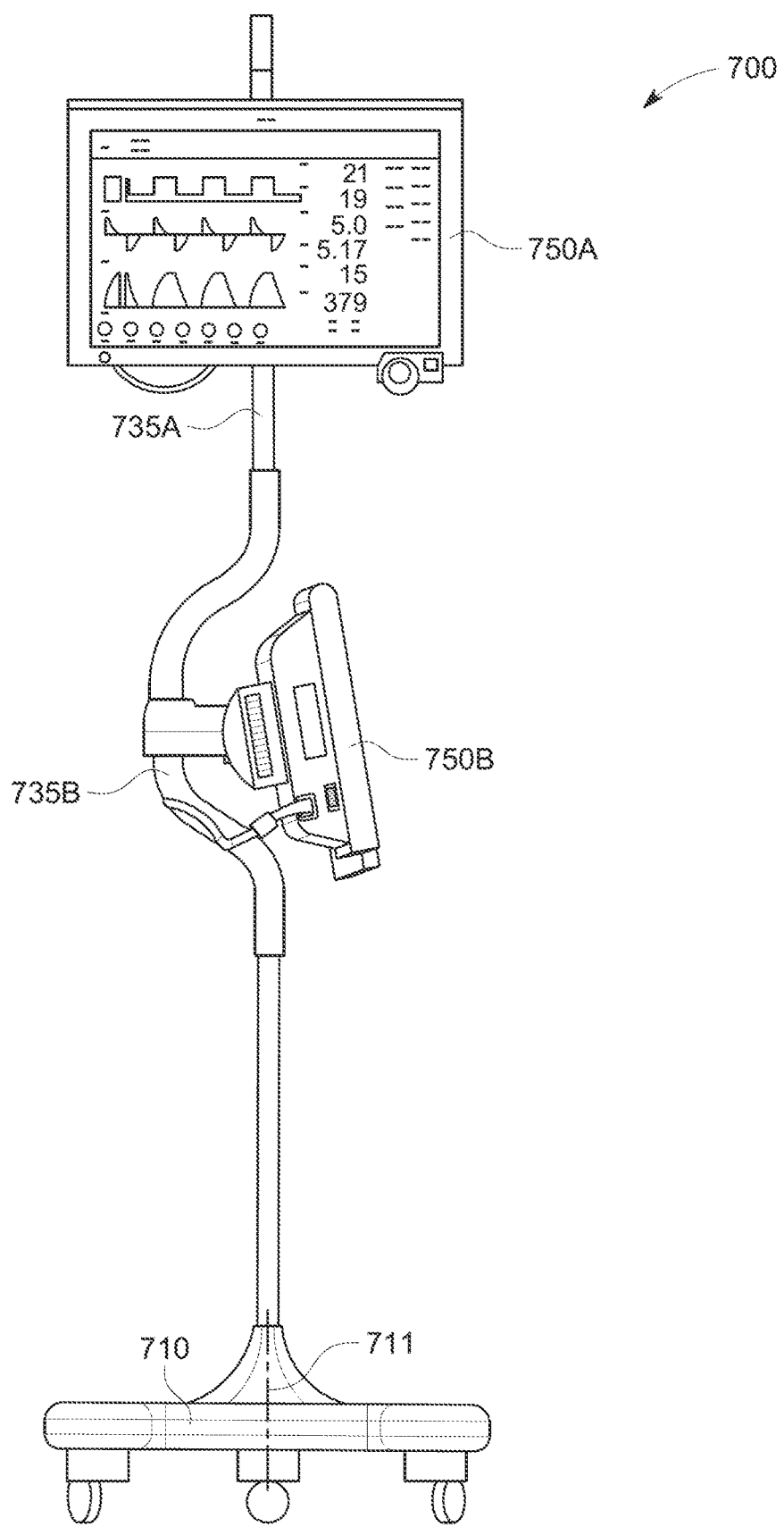
FIG. 7 is a view of an ambulatory medical device stand having multiple medical devices, each with a different orientation, mounted thereto.

As shown in FIG. 7, some embodiments of a medical device stand 700 comprise medical devices 750A, 750B mounted at orientations in azimuth different from each other. In some embodiments not shown, the orientation in elevation may differ. In some embodiments not shown, orientation in both azimuth and elevation may differ. In the embodiment depicted, each medical device 750A, 750B is mounted to a corresponding mounting portion 735A, 735B with a respective horizontal offset from the geometric centroid 711 of base 710.

In some cases, power cords, tubing lines, electrical communication wire, and other similar lines may extend from the various medical devices mounted on a medical device stand. In some embodiments of the present disclosure, conduit, cord organizers, or the like are integrated into the medical device stand.

Figure 8:
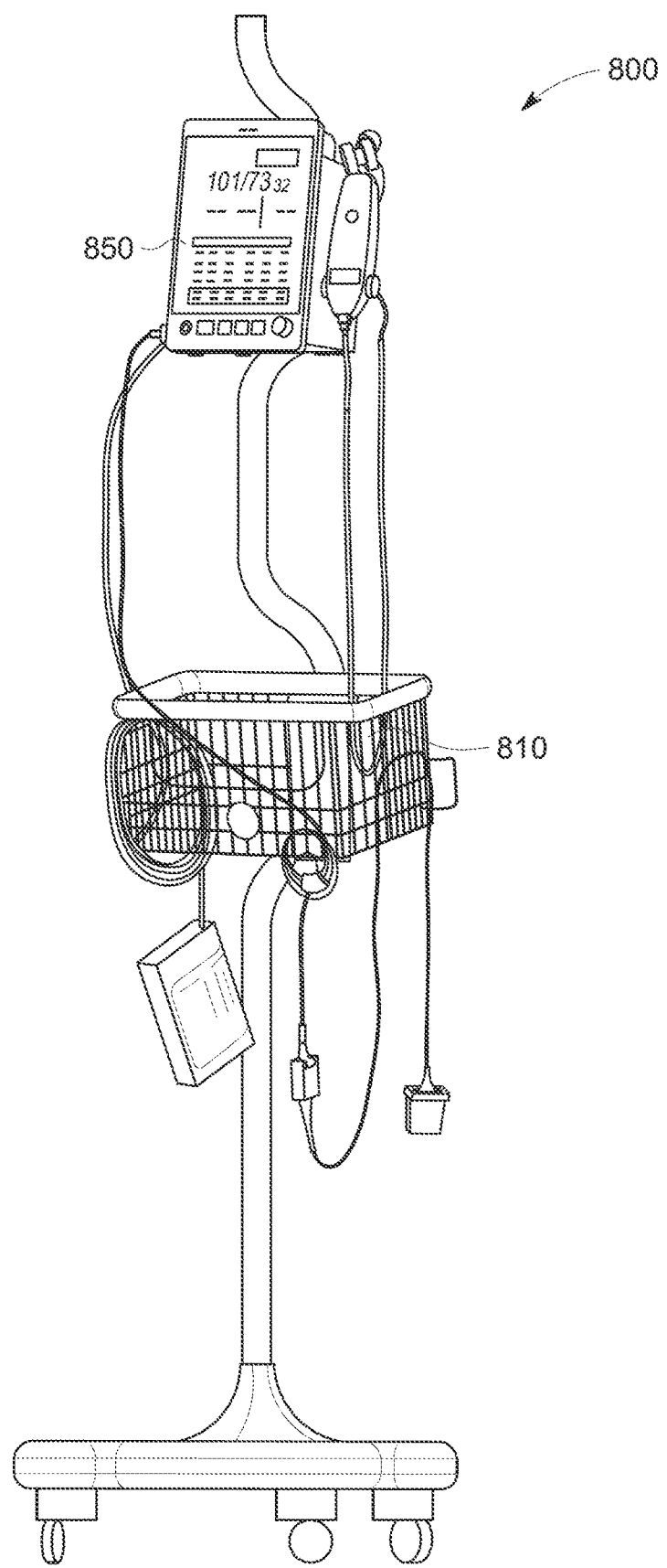
FIG. 8 is a perspective view of an ambulatory medical device stand having a medical device and a utility basket mounted thereto.

Referring now to FIG. 8, one embodiment of a medical device stand 800 includes mounting locations for ancillary items, such as a utility basket 810, in addition to a medical device 850. Other embodiments may include like items such as shelves, trays, push/pull handles, or other items as may be useful and/or appropriate. As used in the present disclosure, such ancillary items are considered a type of medical device when attached to a medical device stand for the purpose of determining a gravitational centroid as described throughout the present disclosure.

Figure 9:
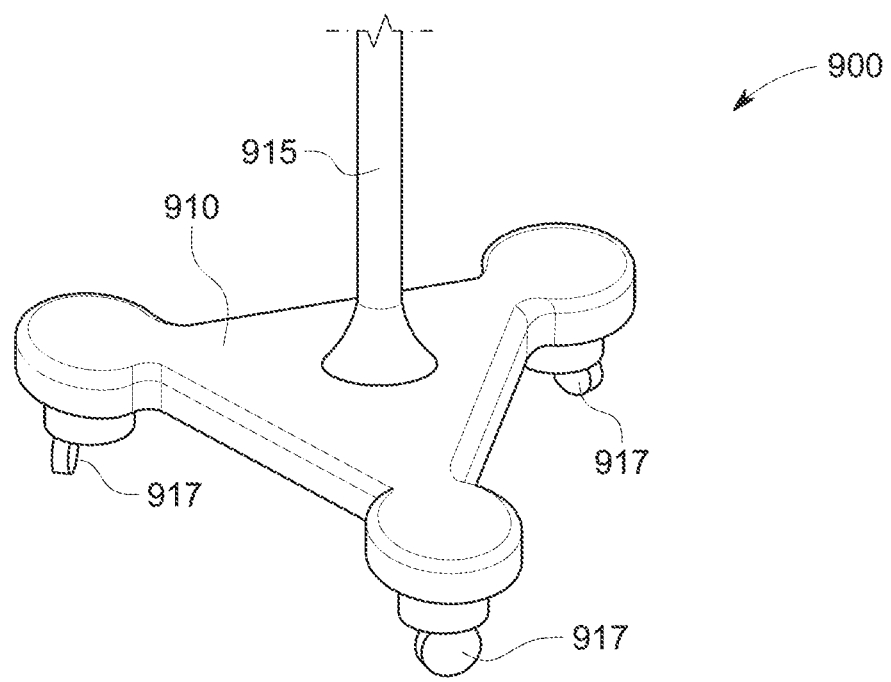
FIG. 9 is a perspective view of a medical device stand base having three casters.
Figure 10:
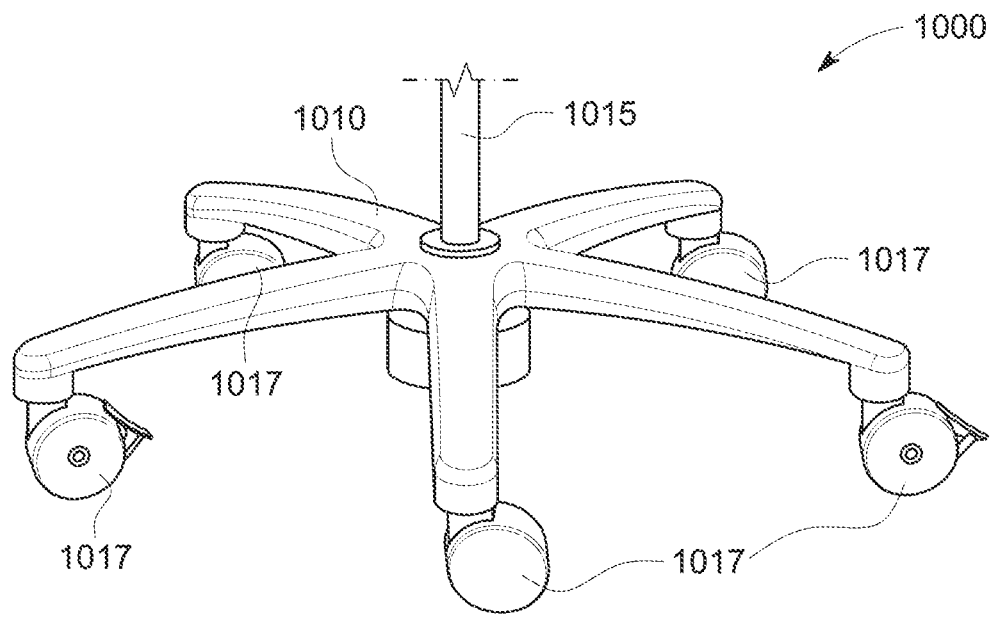
FIG. 10 is a perspective view of a medical device stand base having five casters.

FIGS. 9 and 10 depict variations of a base for a medical device stand according to embodiments of the present disclosure. One embodiment of a medical device stand 900 comprises a base 910 having three casters 917. Another embodiment of a medical device stand 1000 comprises a base 1010 having five casters 1017. Bases 910, 1010 are defined by a base stability region having casters 917, 1017 as vertices. In one embodiment, vertical extensions 915, 1015 extend vertically from the geometric centroid of the base stability region. The respective gravitational centroids of upright supports and medical devices (not pictured) mounted on medical device stands 900, 1000 may be substantially vertically aligned with the geometric centroid of each base 910, 1010, respectively.

According to embodiments of the present disclosure, one or more components of a medical device stand described herein, including base, vertical extension, upright support, connecting member, and mounting member, are manufactured from selected materials having sufficient strength, rigidity, durability, and density to carry out their respective functions described in this disclosure. As examples, components of a medical device stand may be manufactured from steel, aluminum, other metals, alloys, or combinations thereof. Some embodiments comprise one or more elements made from thermoplastics or other polymer materials. In some embodiments, one or more components of a medical device stand described herein, including vertical extension, upright support, connecting member, and mounting member, comprise hollow tubular elements. In some embodiments, components of a medical device stand may be coated with chrome or other protective layers.

As would be understood by a person of ordinary skill in the art having the benefit of the present disclosure, embodiments disclosed herein may present advantages over prior art medical device stands. In particular, embodiments disclosed herein may exhibit increased stability for a given medical device stand weight and base width. Accordingly, embodiments of the present disclosure may result in a medical device stand that is less cumbersome to maneuver and less likely to tip or to tilt.

This concludes the detailed description. The particular examples disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular examples disclosed above may be altered or modified and all such variations are considered within the scope and spirit of the invention. Accordingly, the protection sought herein is as set forth in the claims below.

What is claimed is:

1. A mobile, ambulatory medical device stand for a medical device, the medical device stand comprising:
   an upright support defining a mounting portion upon which a medical device may be mounted, the upright support having a gravitational centroid defined as a combined center of gravity of the upright support and the medical device;
   a base from which the upright support vertically extends; and
   at least three casters structurally engaged with the base, the casters defining a horizontal plane and a geometric centroid, the geometric centroid being substantially vertically aligned with the gravitational centroid of the upright support,
   wherein the mounting portion of the upright support is horizontally offset from the geometric centroid.

2. The medical device stand of claim 1, wherein the geometric centroid is vertically aligned with the gravitational centroid of the upright support.

3. The medical device stand of claim 1, wherein the mounting portion of the upright support is substantially vertical.

4. The medical device stand of claim 1, further comprising a second upright support defining a second mounting portion upon which a second medical device may be mounted, the second upright support having a second gravitational centroid defined as a combined center of gravity of the second upright support and the second medical device, the geometric centroid being substantially vertically aligned with the second gravitational centroid of the second upright support.

5. The medical device stand of claim 4, wherein the second mounting portion is horizontally offset from the geometric centroid.

6. The medical device stand of claim 4, wherein the second mounting portion is substantially vertical.

7. The medical device stand of claim 1, further comprising a second upright support defining a second mounting portion upon which a second medical device may be mounted, the gravitational centroid further defined as a combined center of gravity of the upright support, the medical device, the second upright support, and the second medical device, the geometric centroid being substantially vertically aligned with the gravitational centroid of the upright support.

8. The medical device stand of claim 1, wherein the medical device stand is part of a medical device stand assembly, the medical device stand assembly comprising:
   the medical device stand and
   the medical device mounted to the mounting portion of the medical device stand.

9. A method of assembling a medical apparatus, comprising:
   providing a mobile, ambulatory stand for a medical device, the stand comprising:
      an upright support defining a mounting portion upon which the medical device may be mounted;
      a base, the upright support vertically extending from the base; and
      at least three casters structurally engaged with the base, the casters defining a horizontal plane and a geometric centroid, the mounting portion being horizontally offset from the geometric centroid; and
   mounting the medical device to the mounting portion, such that the medical device and the upright support combine to form a gravitational centroid defined as a combined center of gravity of the upright support and the medical device, the geometric centroid being substantially vertically aligned with the gravitational centroid.

10. The method of claim 9, wherein providing the mobile, ambulatory stand for the medical device comprises:
    arranging the mounting portion and the base to have a horizontal offset between the mounting portion and the geometric centroid, the horizontal offset such that the gravitational centroid is substantially vertically aligned with the geometric centroid while the medical device is mounted to the mount.

11. The method of claim 9, wherein:
    providing the mobile, ambulatory stand for the medical device further comprises providing a second upright support assembled to the first upright support, the second upright support defining a second mounting portion upon which a second medical device may be mounted and
    the method further comprises mounting the second medical device to the second mounting portion, such that the second medical device and the second upright support combine to form a second gravitational centroid defined as a combined center of gravity of the second upright support and the second medical device, the geometric centroid being substantially vertically aligned with the second gravitational centroid.

12. The method of claim 9, wherein:
    providing the mobile, ambulatory stand for the medical device further comprises providing a second upright support assembled to the first upright support, the second upright support defining a second mounting portion upon which a second medical device may be mounted and
    the method further comprises mounting the second medical device to the second mounting portion, such that the medical device, the upright support, the second medical device, and the second upright support combine to form a second gravitational centroid defined as a combined center of gravity of the medical device, the upright support, the second medical device, and the second upright support, the geometric centroid being substantially vertically aligned with the second gravitational centroid.

13. A mobile, ambulatory medical device stand assembly, comprising:
    an upright support defining a mounting portion upon which a medical device may be mounted;
    a medical device mounted at the mounting portion;

a first gravitational centroid defined as a combined center of gravity of the upright support and the medical device;

a base, the upright support vertically extending from the base;

at least three casters structurally engaged with the base, the casters defining a horizontal plane and a geometric centroid, the geometric centroid being substantially vertically aligned with the gravitational centroid of the upright support, wherein the mounting portion is horizontally offset from the geometric centroid.

14. The medical device stand assembly of claim 13, wherein the geometric centroid is vertically aligned with the gravitational centroid of the upright support.

15. The medical device stand assembly of claim 13, wherein the mounting portion is substantially vertical.

16. The medical device stand assembly of claim 13, further comprising a second upright support defining a second mounting portion upon which a second medical device may be mounted, the second upright support having a second gravitational centroid defined as a combined center of gravity of the second upright support and the second medical device, the geometric centroid being substantially vertically aligned with the second gravitational centroid of the second upright support.

17. The medical device stand assembly of claim 16, wherein the second mounting portion is horizontally offset from the geometric centroid.

18. The medical device stand assembly of claim 16, wherein the second mounting portion is substantially vertical.

* * * * *